US011915808B1

(12) United States Patent
Uribe

(10) Patent No.: US 11,915,808 B1
(45) Date of Patent: Feb. 27, 2024

(54) PRIVACY-PRESERVING DNA/RNA/MICROBIOME/COVID-19 TEST KIT KIOSK AND LOCKER THAT PAIRS TO AND STORES RESULTS DATA IN PRIVATE DIGITAL WALLET

(71) Applicant: Daniel Francisco Uribe, Palo Alto, CA (US)

(72) Inventor: Daniel Francisco Uribe, Palo Alto, CA (US)

(*) Notice: Subject to any disclaimer, the term of this patent is extended or adjusted under 35 U.S.C. 154(b) by 825 days.

(21) Appl. No.: 17/033,478

(22) Filed: Sep. 25, 2020

Related U.S. Application Data

(60) Provisional application No. 62/878,585, filed on Jul. 25, 2019.

(51) Int. Cl.
*G16H 10/65* (2018.01)
*A61B 10/00* (2006.01)
(Continued)

(52) U.S. Cl.
CPC ......... *G16H 10/65* (2018.01); *A61B 10/0096* (2013.01); *G01B 21/08* (2013.01);
(Continued)

(58) Field of Classification Search
None
See application file for complete search history.

(56) References Cited

U.S. PATENT DOCUMENTS

2015/0134107 A1* 5/2015 Hyde ............... G16H 20/13
700/237
2019/0385741 A1* 12/2019 Anglada Cortes ..... G16H 15/00
(Continued)

OTHER PUBLICATIONS

Young SD, Klausner J, Fynn R, Bolan R. Electronic vending machines for dispensing rapid HIV self-testing kits: a case study. AIDS Care. Feb. 2014;26(2):267-9. doi: 10.1080/09540121.2013.808732. Epub Jun. 18, 2013. PMID: 23777528; PMCID: PMC3917319. (Year: 2013).*
(Continued)

*Primary Examiner* — Katherine Kolosowski-Gager
(74) *Attorney, Agent, or Firm* — Plager Schack LLP; Mark H. Plager; Stephen Hallberg

(57) ABSTRACT

A privacy-preserving biospecimen test kit kiosk and locker that pairs to and stores data in a private digital wallet is disclosed. The privacy-preserving biospecimen test kit kiosk and locker helps customers to buy DNA/RNA/microbiome/COVID-19 test kits in public places without revealing their identities by pairing with a private digital wallet (smartphone) to allow access and control of their data. The kiosk has a camera for scanning test kit information and capturing palm print images, GPS, environment sensors, a scale, a height meter, and other sensors and provenance gathering devices. The privacy-preserving biospecimen test kit kiosk and locker also serves as a locker to store the DNA/RNA/microbiome/COVID-19 kits. By using the privacy-preserving biospecimen test kit kiosk and locker, users can buy a DNA/RNA/microbiome/COVID-19 test kit, gather information about their bodies and control access to the data by way of their personal and private digital wallets.

10 Claims, 6 Drawing Sheets

(51) Int. Cl.
*G01B 21/08* (2006.01)
*G01G 19/44* (2006.01)
*G01K 13/00* (2021.01)
*G01N 33/00* (2006.01)
*G01S 19/01* (2010.01)
*G06F 3/16* (2006.01)
*G06F 16/00* (2019.01)
*G06F 21/62* (2013.01)
*G06K 7/10* (2006.01)
*G06Q 10/087* (2023.01)
*G06Q 20/18* (2012.01)
*G06Q 20/20* (2012.01)
*G06Q 20/36* (2012.01)
*G06Q 20/38* (2012.01)
*G06Q 20/40* (2012.01)
*G06Q 30/018* (2023.01)
*G06Q 50/26* (2012.01)
*G06V 40/13* (2022.01)
*G06V 40/50* (2022.01)
*G10L 17/04* (2013.01)
*G16H 10/40* (2018.01)
*G16H 40/20* (2018.01)
*G16H 40/67* (2018.01)
*H04L 9/06* (2006.01)
*H04L 9/08* (2006.01)
*H04L 9/32* (2006.01)
*G06F 3/0481* (2022.01)
*G06F 3/04883* (2022.01)
*H04L 9/00* (2022.01)

(52) U.S. Cl.
CPC ............. *G01G 19/44* (2013.01); *G01K 13/00* (2013.01); *G01N 33/0004* (2013.01); *G01S 19/01* (2013.01); *G06F 3/167* (2013.01); *G06F 16/00* (2019.01); *G06F 21/6245* (2013.01); *G06K 7/10297* (2013.01); *G06Q 10/087* (2013.01); *G06Q 20/18* (2013.01); *G06Q 20/206* (2013.01); *G06Q 20/208* (2013.01); *G06Q 20/363* (2013.01); *G06Q 20/3672* (2013.01); *G06Q 20/3674* (2013.01); *G06Q 20/383* (2013.01); *G06Q 20/40145* (2013.01); *G06Q 30/0185* (2013.01); *G06Q 50/265* (2013.01); *G06V 40/1318* (2022.01); *G06V 40/50* (2022.01); *G10L 17/04* (2013.01); *G16H 10/40* (2018.01); *G16H 40/20* (2018.01); *G16H 40/67* (2018.01); *H04L 9/0637* (2013.01); *H04L 9/0643* (2013.01); *H04L 9/0866* (2013.01); *H04L 9/3213* (2013.01); *G06F 3/0481* (2013.01); *G06F 3/04883* (2013.01); *G06Q 2220/00* (2013.01); *H04L 9/50* (2022.05)

(56) References Cited

U.S. PATENT DOCUMENTS

| | | | |
|---|---|---|---|
| 2020/0076798 A1* | 3/2020 | Lidsky | H04L 9/3228 |
| 2021/0350648 A1* | 11/2021 | Lodha | G06Q 20/40145 |
| 2022/0139566 A1* | 5/2022 | Gardina | G16B 50/20 |
| | | | 705/2 |

OTHER PUBLICATIONS

"How Blockchain Makes a Smart Lock Even Smarter" available at: https://medium.com/coreledger/how-blockchain-makes-a-smart-lock-even-smarter-520d01176f4b, accessed Oct. 2023 (Year: 2019).*

* cited by examiner

PRIVACY-PRESERVING DNA/RNA/MICROBIOME/COVID-19 TEST KIT KIOSK AND LOCKER THAT PAIRS TO AND STORES RESULTS DATA IN PRIVATE DIGITAL WALLET

CLAIM OF BENEFIT TO PRIOR APPLICATION

This application claims benefit to U.S. Provisional Patent Application 62/878,585, entitled "PRIVACY-PROTECTING DNA/RNA/MICROBIOME TEST KIT KIOSK AND LOCKER THAT PAIRS TO AND STORES RESULTS DATA IN PRIVATE DIGITAL WALLET," filed Jul. 25, 2019. The U.S. Provisional Patent Application 62/878,585 is incorporated herein by reference.

BACKGROUND

Embodiments of the invention described in this specification relate generally to privacy protection or preservation of identity in distribution and collection of items, and more particularly, to a privacy-preserving DNA/RNA/microbiome/COVID-19 test kit kiosk and locker that pairs to and stores retrieved data in a personal wallet, such as a private digital wallet or a paper or card-based wallet.

Many consumers want to remain private/anonymous to the outside world when buying DNA/RNA/microbiome/COVID-19 test kits, and therefore, they do not want to disclose identifying information, such as their address, their email, other personal data, etc. Existing health kiosks do not enable users to deposit their bio-samples inside a kit and do not respect or maintain user privacy as the existing kiosks retrieve and store identity data.

Furthermore, when a consumer buys a DNA/RNA/microbiome/COVID-19 test kit, there are a lot of conditions and other information which could be recorded or captured, such as location, time and date, detectable health and bodily composition measurements of the purchaser, environmental conditions at the location of purchase, etc., but which are completely disregarded in the commercial spaces currently available to purchase any such DNA/RNA/microbiome/COVID-19 test kits. Although it is possible to gather metadata (or "provenance data") about such conditions associated with a purchase of a DNA/RNA/microbiome/COVID-19 test kit, none of the existing options do so. Thus, when a DNA/RNA/microbiome/COVID-19 test kit is purchased in a drug store or pharmacy, all the provenance data is lost. As a consequence of losing the provenance data, the resulting data from processing of a biospecimen is not as valuable as data that includes provenance data, such as, for example, height of the consumer, weight of the consumer, air quality at the location of purchase, humidity at the location, time and date of purchase, GPS location data, heartbeat of the consumer, etc.

Therefore, what is needed is a kiosk that helps customers to buy DNA/RNA/microbiome/COVID-19 test kits in public places without revealing their identities but which allows customers to gather information about their bodies and provide it to a lab for processing and where a donor's personal and private digital wallet (accessible via their smartphone) or other personal wallet (paper or card-based wallet) enable the donor to control access to their bodily information and the post-processed data that results from lab processing of the bodily information, while also capturing provenance data by way of location sensors (GPS), environment sensors, a weight scale, a height meter, and other sensors.

BRIEF DESCRIPTION

A novel privacy-preserving DNA/RNA/microbiome/COVID-19 biospecimen test kit kiosk and locker is disclosed that pairs to and stores retrieved data in a personal wallet, where the personal wallet is a private digital wallet, a paper-based wallet, or a card-based wallet. In some embodiments, the privacy-preserving DNA/RNA/microbiome/COVID-19 biospecimen test kit kiosk and locker (hereinafter also referred to as "biospecimen test kit kiosk and locker") helps customers to buy DNA/RNA/microbiome/COVID-19 biospecimen test kits (hereinafter also referred to in singular form as "biospecimen test kit" and in plural form as "biospecimen test kits") in public places without revealing their identities. In some embodiments, the privacy-preserving biospecimen test kit kiosk and locker pairs with the personal wallet (private digital wallet, paper-based wallet, or card-based wallet) of each customer (or "donor"), thereby allowing customers to obtain test kits from the kiosk in order to gather information about their bodies (in the form of biospecimen samples) and store the biospecimen samples in physical lockers of the kiosk, with each locker functioning as (i) a physical collection repository of a donor's biospecimen sample to deliver to a processing lab and (ii) a logical session portal to the donor's personal wallet, which when accessed by private key (digital, paper, or card-based) enables the donor to open and close sessions to control access to their information including the biospecimen sample and any post-processed data that results from lab processing of the donor's biospecimen. In some embodiments, the privacy-preserving biospecimen test kit kiosk and locker enables portal access to the data by way of the paired personal wallet (digital wallet, paper wallet, or card-based wallet) of a user, thereby enabling the user (donor) to authorize access to their data, revoke access to their data, request biospecimen destruction, and otherwise control who has access to user's data and bodily information, what data and bodily information is accessible, and how the user's data and bodily information can be used, while maintaining complete privacy of the identity and identifying information of the user (donor). In some embodiments, the privacy-preserving biospecimen test kit kiosk and locker also includes a camera, a palm print scanner processing module that scans an image of a palm of the donor captured by the camera, GPS, environment sensors, a near field communication (NFC) card reader, a scale, and a height meter.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having thus described the invention in general terms, reference is now made to the accompanying drawings, which are not necessarily drawn to scale, and which show different views of different example embodiments.

Figure 1:
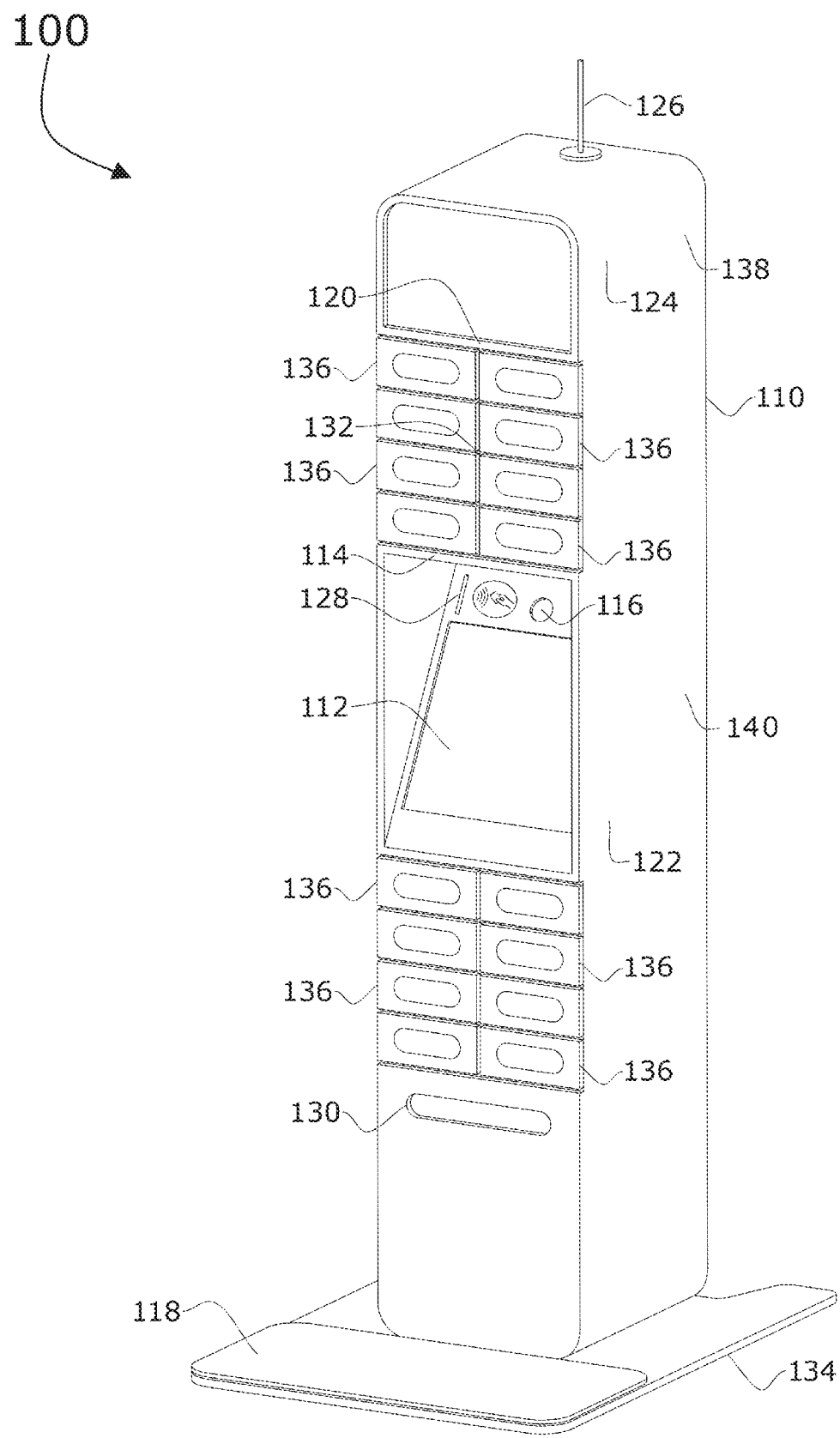

FIG. 1 conceptually illustrates a perspective view of a privacy-preserving biospecimen test kit kiosk and locker in some embodiments.

Figure 2:
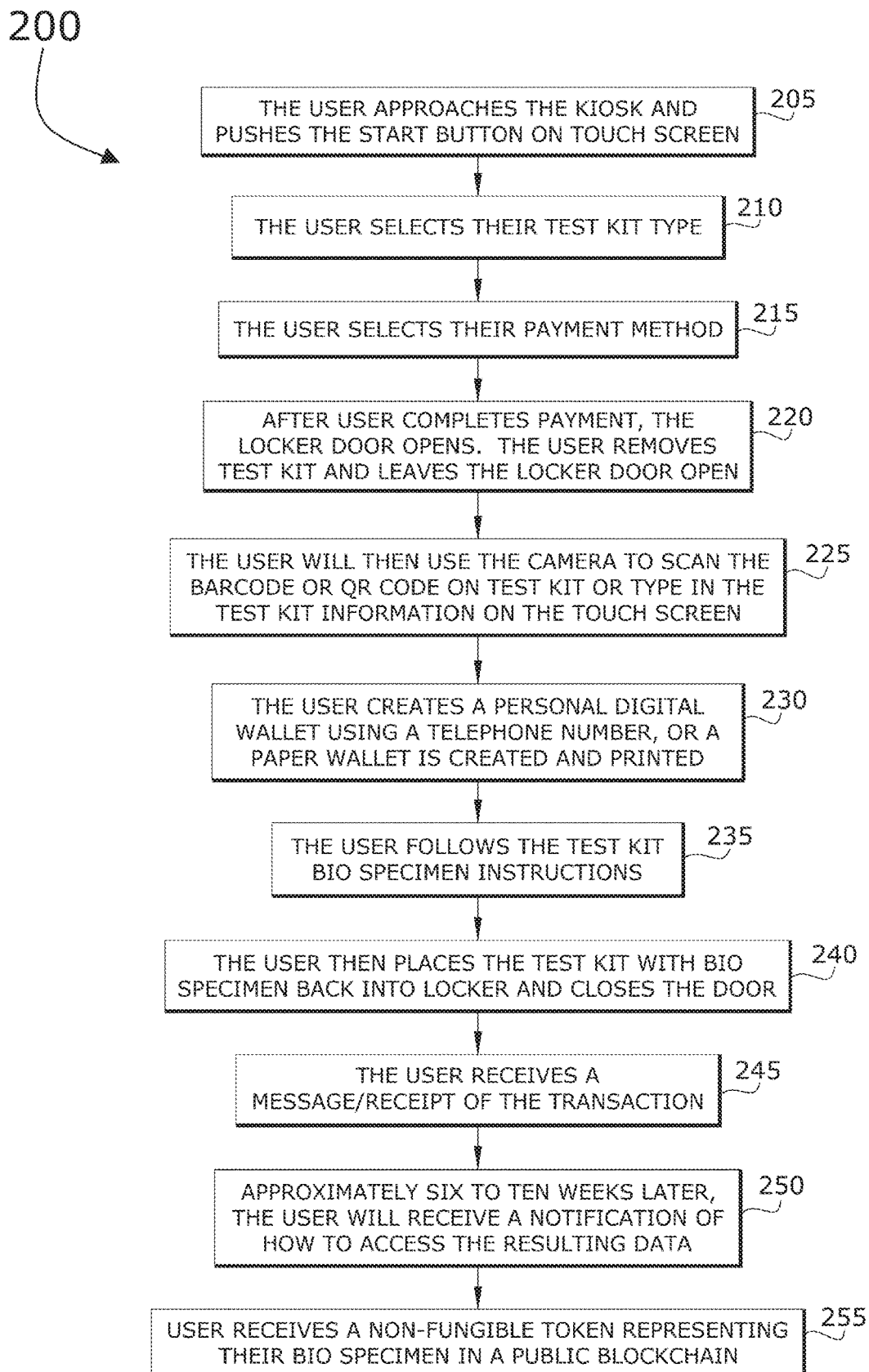

FIG. 2 conceptually illustrates a privacy-preserving biospecimen test kit purchase and personal biospecimen providing process for obtaining a biospecimen test kit at a privacy-preserving biospecimen test kit kiosk and locker to provide a personal biospecimen for lab processing while capturing provenance data and protecting identity of the donor of the personal biospecimen in some embodiments.

Figure 3:
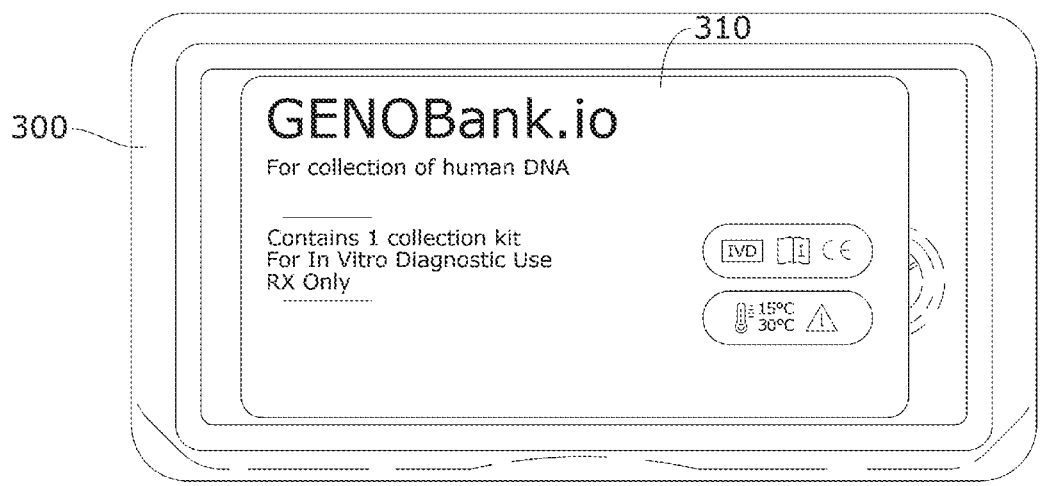

FIG. 3 conceptually illustrates a top view of a biospecimen test kit stored in each locker of the privacy-preserving biospecimen test kit kiosk and locker in some embodiments.

Figure 4:
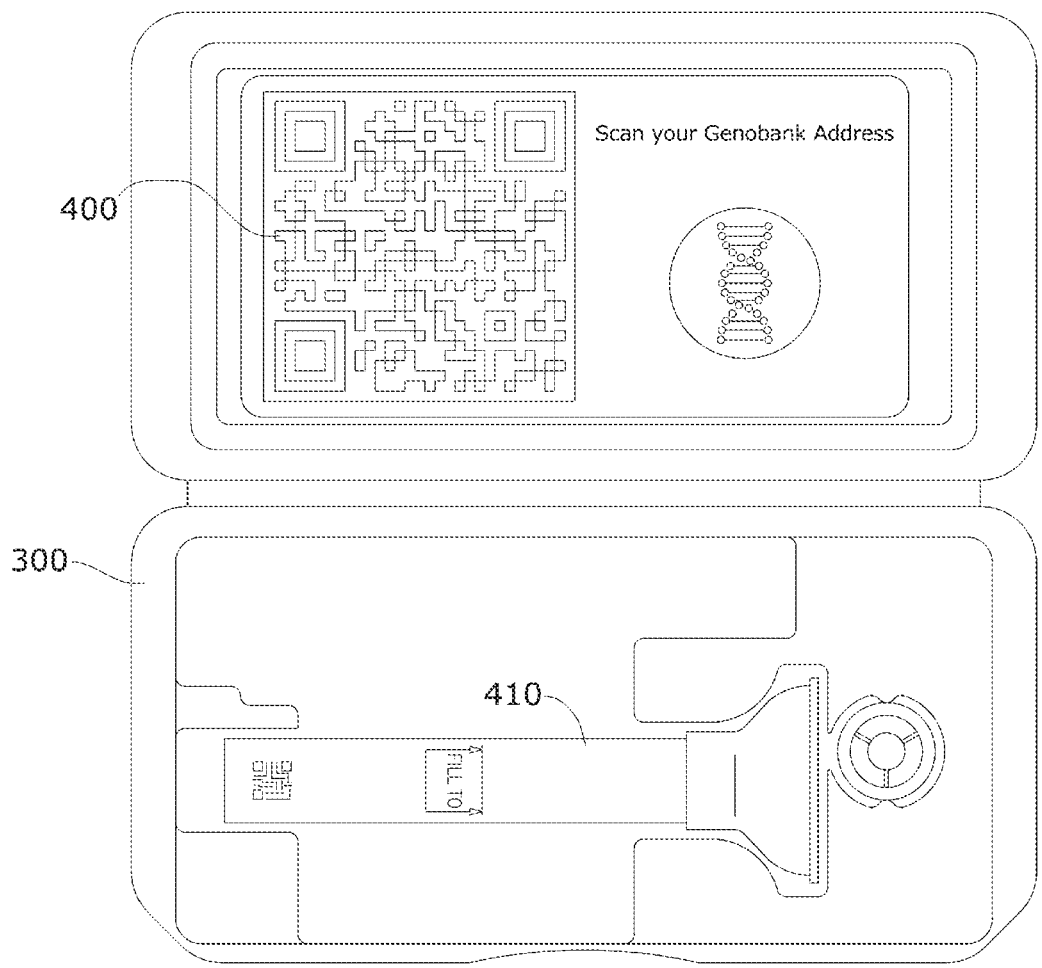

FIG. 4 conceptually illustrates a top view of a unique scannable code associated with the biospecimen test kit shown in FIG. 3.

Figure 5:
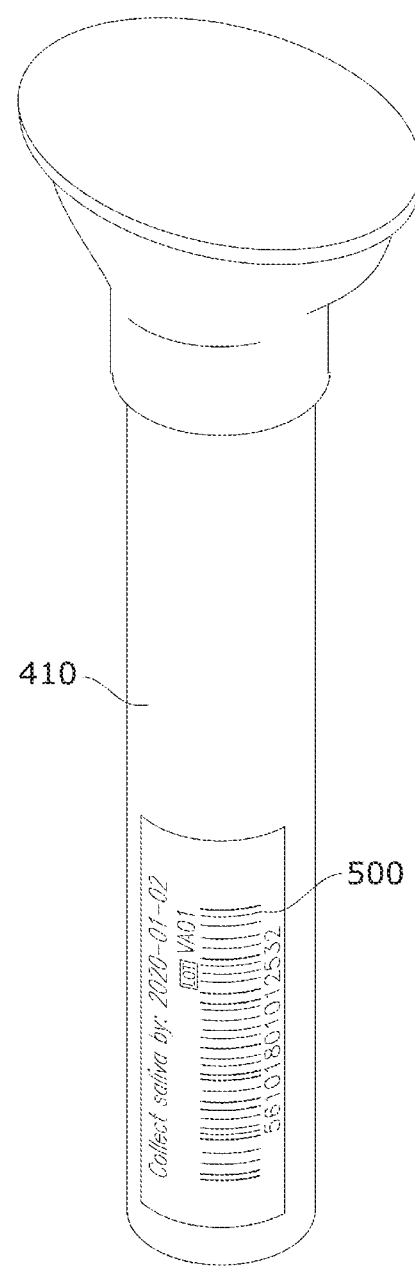

FIG. 5 conceptually illustrates a rear perspective view of a biospecimen collection tube in some embodiments with a collection tube identifying sticker affixed to an outer surface of the biospecimen collection tube.

Figure 6:
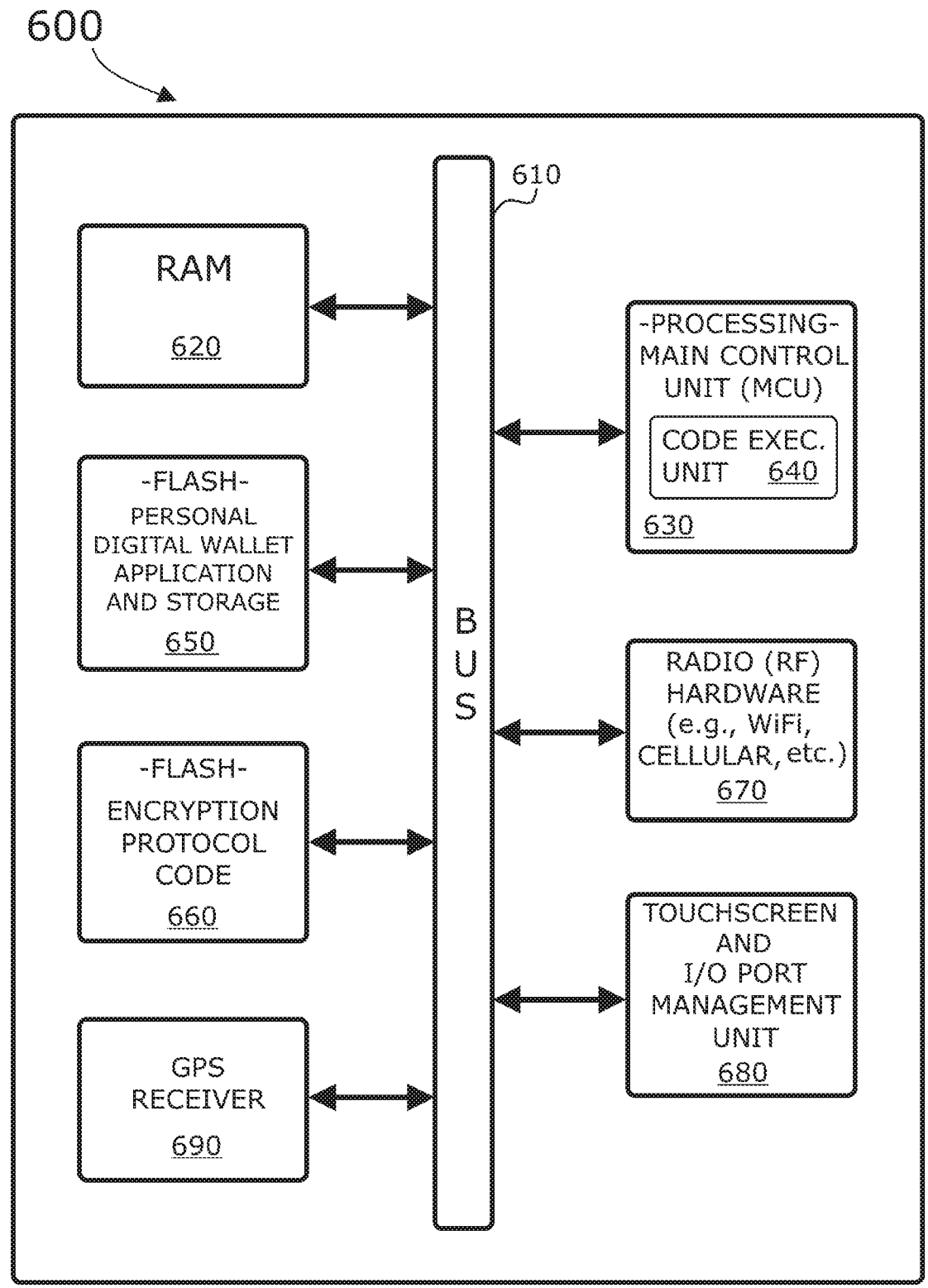

FIG. 6 conceptually illustrates a block diagram of a mobile device with a personal digital wallet for a user of the privacy-preserving biospecimen test kit kiosk and locker in some embodiments.

Figure 7:
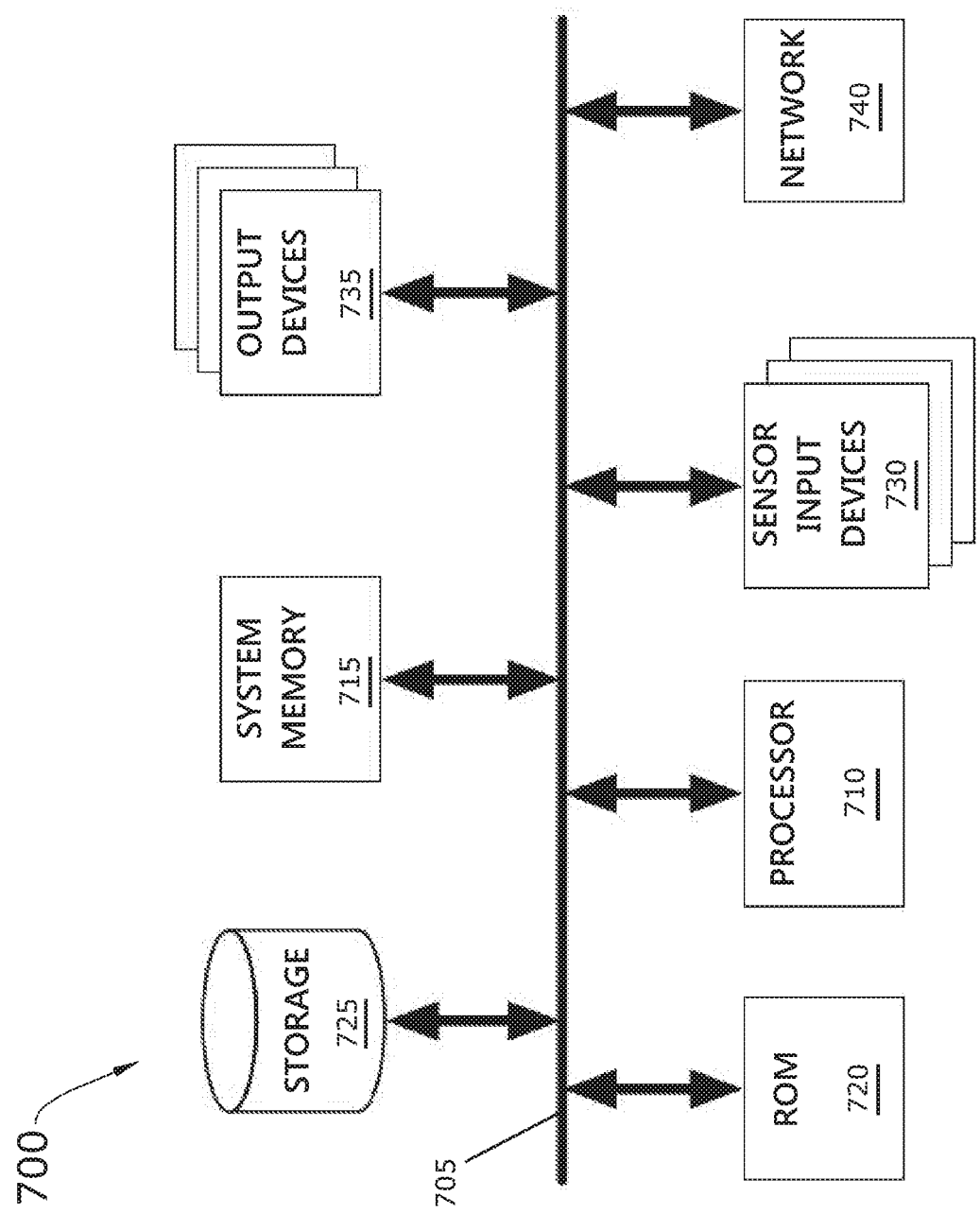

FIG. 7 conceptually illustrates an electronic system with which some embodiments of the invention are implemented.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

In this specification, the phrase "data provenance" refers to records of the inputs, entities, systems, and processes that influence data of interest. Similarly, the phrase "provenance data" is used throughout this specification to refer to data and metadata collected before, during, or after collection of biospecimen and bio-samples that are processed to derive resulting data of interest. Examples of provenance data include, without limitation, time and date of obtaining a biospecimen test kit, time and date of securing a biospecimen sample in a collection tube of a biospecimen test kit, air quality, temperature, and humidity measurements in and around a privacy-preserving biospecimen test kit kiosk and locker used to obtain a biospecimen test kit and store biospecimen samples, location of the privacy-preserving biospecimen test kit kiosk and locker from which a user obtains a biospecimen test kit and stores a user-provided biospecimen sample, etc. The data of interest in this specification refers to data derived from human bio-samples or biospecimen samples. Examples of data of interest include DNA and RNA from human saliva biospecimen samples, microbiome data and probiotic profile data from human waste samples (e.g., stool samples, feces, etc.), infectious disease data from human nasal mucus samples, etc.

Some embodiments of the invention include a novel privacy-preserving biospecimen test kit kiosk and locker that pairs to and stores retrieved data in a personal wallet, where the personal wallet is a private digital wallet, a paper-based wallet, or a card-based wallet. In some embodiments, the privacy-preserving biospecimen test kit kiosk and locker helps customers to buy biospecimen test kits in public places without revealing their identities or identifying information. In some embodiments, the privacy-preserving biospecimen test kit kiosk and locker pairs with the personal wallet (private digital wallet, paper-based wallet, or card-based wallet) of each customer (or "donor"), thereby allowing customers to obtain test kits from the kiosk in order to gather information about their bodies (in the form of biospecimen samples) and store the biospecimen samples in physical lockers of the kiosk, with each locker functioning as (i) a physical collection repository of a donor's biospecimen sample to deliver to a processing lab and (ii) a logical session portal to the donor's personal wallet, which when accessed by private key (digital, paper, or card-based) enables the donor to open and close sessions to control access to their information including the biospecimen sample and any post-processed data that results from lab processing of the donor's biospecimen. In some embodiments, the privacy-preserving biospecimen test kit kiosk and locker enables portal access to the data by way of the paired personal wallet (digital wallet, paper wallet, or card-based wallet) of a user, thereby enabling the user (donor) to authorize access to their data, revoke access to their data, request biospecimen destruction, and otherwise control who has access to user's data and bodily information, what data and bodily information is accessible, and how the user's data and bodily information can be used, while maintaining complete privacy of the identity and identifying information of the user (donor). In some embodiments, the privacy-preserving biospecimen test kit kiosk and locker also includes a camera, a palm print scanner processing module that scans an image of a palm of the donor captured by the camera, GPS, environment sensors, a near field communication (NFC) card reader, a scale, and a height meter.

As stated above, consumers typically want to remain private/anonymous to the outside world when buying biospecimen test kits, and therefore, they do not want to disclose identifying information, such as their address, their email, other personal data, etc. Existing health kiosks do not enable users to deposit their bio-samples inside a kit and do not respect or maintain user privacy as the existing kiosks retrieve and store identity data. Furthermore, when a consumer buys a biospecimen test kit, there is a lot of provenance data which could be recorded or captured, but which are completely disregarded in the commercial spaces currently available to purchase any such biospecimen test kits. Thus, when a biospecimen test kit is purchased in a drug store or pharmacy, all the provenance data that could be captured is lost. As a consequence of losing the provenance data, the resulting data from processing of a donor-provided biospecimen is not as valuable as data that includes provenance data, such as, for example, height of the consumer donor, weight of the consumer donor, air quality, temperature, and humidity at the location of purchase, time and date of purchase, GPS location data, heartbeat of the consumer donor, etc. Embodiments of the privacy-preserving biospecimen test kit kiosk and locker described in this specification solve such problems by allowing users to purchase a biospecimen test kit, gather personal body data (biospecimen samples) in private, and provide the resulting test kit-obtained biospecimen samples to a lab for processing, and maintain access and control over the biospecimen and data resulting from lab processing of the biospecimen via the personal private digital wallet (or paper wallet or card-based wallet) without associating or revealing their identities. Furthermore, having all the metadata that describes the provenance of the biosample makes it valuable for researchers and helps to corroborate its authenticity.

Embodiments of the privacy-preserving biospecimen test kit kiosk and locker described in this specification differ from and improve upon currently existing options. In particular, some embodiments differ from existing kits which people use but have to risk their identity (and privacy) or are required to become a "patient" in the conventional sense to buy and perform a DNA test, a RNA test, a microbiome test, a COVID-19 test, or another test based on lab processing of a biospecimen. In contrast, consumers (users) of the privacy-preserving biospecimen test kit kiosk and locker can buy a biospecimen test kit, gather information about their bodies for lab processing, access data resulting from lab processing, and control access to their data and biospecimen samples by way of their personal and private digital wallets (or paper wallets or card-based wallets), thus ensuring that these users will own and control access to their data and can keep track of their biospecimen sample(s), as well as be able to enrich the biospecimen with provenance metadata, all with the guarantee of privacy by receiving the results of the biosample test in their private and personal digital wallet.

The privacy-preserving biospecimen test kit kiosk and locker of the present disclosure may be comprised of the following elements. This list of possible constituent elements is intended to be exemplary only and it is not intended that this list be used to limit the privacy-preserving biospecimen test kit kiosk and locker of the present application to just these elements. Persons having ordinary skill in the art relevant to the present disclosure may understand there to be equivalent elements that may be substituted within the present disclosure without changing the essential function or operation of the privacy-preserving biospecimen test kit kiosk and locker.

1. Metal body housing of the privacy-preserving biospecimen test kit kiosk and locker, including multiple biospecimen test kit lockers (small, separated locker boxes with lockable front doors, each locker box including an internal locker sensor to detect presence or absence of a biospecimen test kit inside the locker)
2. Touch screen (or touch-pad) display and interactive user control device
3. Microphone (or microphone and audio speaker combination)
4. Camera
5. Weight scale
6. Height sensor (or height meter)
7. Air quality sensor
8. Humidity sensor
9. GPS sensor
10. Cellular antenna
11. Embedded computing device with CPU, data storage, memory, and other hardware components and/or embedded software modules or programs
12. NFC card reader (NFC implementation for ease of having a pre-established private locker for people who do not understand blockchain and/or private/public key scheme)

The privacy-preserving biospecimen test kit kiosk and locker of the present disclosure generally works by the following steps:

1. A user at the kiosk presses a "Start Button" displayed on the touch screen of the privacy-preserving biospecimen test kit kiosk and locker.
2. The touch screen displays a kit selection screen from which the user is allowed to select a kit from multiple types of biospecimen test kits, including (a) a DNA kit (ancestry, polygenic risk score), (b) an RNA kit (gene expression, epigenetics), (c) a microbiome kit (probiotics profile), and/or (d) a COVID-19 test kit (SARS-CoV-2 RT-PCR).
3. After selection, the user pays for the selected biospecimen test kit (purchases the biospecimen test kit) by any of several payment methods, such as credit card, debit card, digital wallet purchase via smartphone, cryptocurrency payment, or other payment type for the selected biospecimen test kit.
4. After successfully paying for the selected biospecimen test kit, a locker box of the privacy-preserving biospecimen test kit kiosk and locker opens, allowing the user to retrieve the selected and purchased biospecimen test kit. The user leaves the locker box open after removing the biospecimen test kit.
5. On the touch screen, the user is prompted to scan a biospecimen test kit code (such as a QR code or a barcode) by using the camera that is integrated and embedded in the privacy-preserving biospecimen test kit kiosk and locker with a lens of the camera disposed along an outer surface of the metal housing (e.g., near by the touchscreen display). The user interacts with the touchscreen to issue a command for the camera to scan the biospecimen test kit code. A biospecimen test kit code typically includes information such as a numeric or alpha-numeric identifier, a brand, and an expiration date for the biospecimen test kit. The biospecimen test kit code may be printed on a sticker attached to a biospecimen test kit container and/or biospecimen collection tube in the kit, or otherwise legibly printed along an outer surface of the biospecimen test kit container and/or tube. The code is a unique code that is only associated with one particular biospecimen test kit (i.e., the one on which the code is printed). As an alternative to using the camera to scan the code, the user may select a keyboard input option from the touchscreen, which visually outputs a virtual keyboard on the touchscreen, thereby allowing the user to type in the biospecimen test kit information without scanning the code.
6. After scanning the code (or typing the biospecimen test kit information via the keyboard), the user creates a personal digital wallet using at least a telephone number (inputting the telephone number into the touchscreen), or, alternatively, a paper wallet is created and printed (for maximum privacy, when user does not want to create a personal digital wallet using a telephone number) or an NFC card is provided for the user's wallet, such that an NFC card reader of the privacy-preserving biospecimen test kit kiosk and locker can access the wallet when the user taps the NFC card against the NFC card reader.
7. Then the user follows the instructions on the selected and purchased biospecimen test kit and deposits a biospecimen, such as saliva, or another biosample.
8. After depositing the biospecimen in a tube of the biospecimen test kit, the user places the biospecimen test kit (containing the tube with the corresponding biospecimen) in the same locker box and closes the locker box door.
9. A transaction message or receipt is then delivered to the user. If the user created a personal digital wallet using a phone number, the privacy-preserving biospecimen test kit kiosk and locker sends a message to the phone number as a receipt of the transaction. If a paper wallet was created, then the privacy-preserving biospecimen test kit kiosk and locker prints a paper receipt of the transaction, which is printed and output to the user through a printer paper opening of the privacy-preserving biospecimen test kit kiosk and locker. The message/receipt also includes information explaining when and how to retrieve the resulting data after lab processing of the corresponding biosample.

10. Six to ten weeks later, the user receives a notification (if phone number was used to create the personal digital wallet) of how to access the resulting data and/or digital report(s) associated with the biospecimen test kit.

11. The user also receives a non-fungible token (NFT) representing their biospecimen and resulting data in a public blockchain. In some embodiments, the NFT is implemented according to the ERC 721 standard.

By way of example, FIG. 1 conceptually illustrates a perspective view of a privacy-preserving biospecimen test kit kiosk and locker 100. As shown in this figure, the privacy-preserving biospecimen test kit kiosk and locker 100 is constructed with a metal body housing 110 standing upright atop a base 134 (or base plate 134). In some embodiments, the privacy-preserving biospecimen test kit kiosk and locker 100 also includes a touchscreen display 112, a microphone 114, a camera 116, a weight scale 118, a height sensor 120, an air quality sensor 122, a GPS sensor 124, a cellular antenna 126, a card reader with NFC reader 128, a printer paper opening 130, a humidity sensor 132, a plurality of lockers 136, an ambient room temperature sensor 138, and an embedded computing device 140.

As noted above, there is widespread interest among consumers to purchase biospecimen test kits in which personal biospecimen samples can be processed by a lab and access to resulting data provided to such consumers by way of personal wallet (digital, paper, or card-based wallet). For example, many consumers are interested in having a lab process DNA/RNA from a biospecimen, or analyze a biospecimen to determine their microbiome condition. Similarly, many consumers are presently interested in determining whether they have or had COVID-19, or other infectious diseases. A lot of these consumers also wish to remain private/anonymous to the outside world when buying DNA/RNA/microbiome/COVID-19 test kits or when such biospecimen is processed at a lab, but also wish to retain access to and control of their data.

Generally, the privacy-preserving biospecimen test kit kiosk and locker 100 satisfies such consumer privacy/anonymity demands. For instance, a particular consumer (or "user") can approach the privacy-preserving biospecimen test kit kiosk and locker 100 with the intention of purchasing a biospecimen test kit. To do so, the user may need to stand on the weight scale 118, which is disposed above the base 134 and in front of the touchscreen display 112. Then the user starts a process for selecting and purchasing a biospecimen test kit and completing other actions, such as creating a digital wallet and providing the biospecimen to be processed. Starting this process may be as simple as the user interacting with the touchscreen display 112 (e.g., selecting a "Start Button" that is visual output onto the touchscreen display 112), but may alternatively be started by an audible voice command uttered by the user (e.g., "Start"), which is captured by the microphone 114 to trigger the privacy-preserving biospecimen test kit kiosk and locker 100 to start the biospecimen test kit selection and purchase process.

While interacting with the touchscreen display 112 (or audibly interacting via the microphone 114), the user will typically be standing on the weight scale 118. In some embodiments, the privacy-preserving biospecimen test kit kiosk and locker 100 starts capturing provenance data, such as the user's weight via the weight scale 118. Since the user is standing in front of the touchscreen display 112, the privacy-preserving biospecimen test kit kiosk and locker 100 may also detect the user's height via the height sensor 120 which is positioned within the metal body housing 110 at a central location, such as between several lockers 136, as shown in this figure. Additionally, the privacy-preserving biospecimen test kit kiosk and locker 100 may capture GPS location data via the GPS sensor 124, as well as information about air quality via the air quality sensor 122, humidity data via the humidity sensor 132, and ambient room temperature via the ambient room temperature sensor 138.

The provenance data may be captured by the privacy-preserving biospecimen test kit kiosk and locker 100 before or immediately after the user makes a selection of a biospecimen test kit, such as (a) a DNA kit (ancestry, polygenic risk score), (b) an RNA kit (gene expression, epigenetics), (c) a microbiome kit (probiotics profile), and/or (d) a COVID-19 test kit (SARS-CoV-2 RT-PCR). After the biospecimen test kit is selected, the user is presented with instructions to pay for the kit. If the user decides not to pay for the kit, the provenance data is discarded and the privacy-preserving biospecimen test kit kiosk and locker 100 resets the touchscreen display 112 to a default starting position. However, if the user provides verified payment information to purchase the selected biospecimen test kit (e.g., credit card, debit card, digital wallet purchase via smartphone, cryptocurrency payment, or any other valid and accepted payment type), then the privacy-preserving biospecimen test kit kiosk and locker 100 automatically opens a particular locker 136. Inside the particular locker 136 is a biospecimen test kit of the user-selected type. An example of a biospecimen test kit that is stored in the locker 136 is described below, by reference to FIG. 3. On the touchscreen display 112, the user is instructed to take the biospecimen test kit out of the particular locker 136 and leave the locker open so that the biospecimen test kit can be placed back in the particular locker 136 after providing the user's biospecimen sample.

In order to uniquely associate the biospecimen sample and resulting data (after processing at the lab) with the user in a way that retains the user's privacy and anonymity, the biospecimen test kit includes a unique identifying code, such as a QR code, a bar code, or other human-readable information that uniquely identifies the biospecimen test kit purchased by the user and distinguishes from other biospecimen test kits. Although the privacy-preserving biospecimen test kit kiosk and locker 100 does not require the user to reveal his or her identity in conventional ways, the biospecimen test kit and resulting data is paired with (or can otherwise be associated with) a personal wallet (digital wallet, paper wallet, or card-based wallet) which is associated with the user. The privacy-preserving biospecimen test kit kiosk and locker 100 helps the user to set up such a personal wallet (either creating a private personal digital wallet, or alternatively, printing out a paper wallet, or distributing a card-based wallet that can be read by an NFC card scanner), so that access to data results of the user's biospecimen sample can be deposited into donor's encrypted storage linked to the corresponding wallet (public address), represented as a non-fungible token (NFT). Also, this transaction is recorded in a public blockchain without exposing personal data. The privacy-preserving biospecimen test kit kiosk and locker 100 links these together by first instructing the user (on the touchscreen display 112) to scan the code for the biospecimen test kit. The user is instructed to scan the code with the camera 116. The biospecimen test kit code may be printed on a sticker attached to a biospecimen test kit container and/or biospecimen collection tube in the kit, or otherwise legibly printed along an outer surface of the biospecimen test kit packaging container and/or biospecimen collection tube. The code is a unique code that is only associated with one particular biospecimen test kit (i.e., the one on which the code is printed). An example of a biospecimen test kit with a biospecimen test kit code and a biospecimen collection tube is described below, by reference to FIG. 4. In some cases, the user may be prompted to input a numeric code or an alpha-numeric code that is printed or displayed on the biospecimen test kit packaging container and/or the biospecimen collection tube stored within the packaging of the biospecimen test kit packaging container. An example of a biospecimen collection tube with a bar code and a human-readable code that can be input by the user is described below, by reference to FIG. 5.

In some embodiments, the unique code of the biospecimen test kit (along with the brand and expiration date listed on the biospecimen test kit) is used in combination with other data to generate a first non-funigible token (NFT) that represents the biospecimen before the lab processes the bio-sample and derives relevant data results. The other data includes provenance data, such as air quality data as detected by the air quality sensor 122, humidity data as detected by the humidity sensor 132, temperature data as detected by the ambient room temperature sensor 138, the location of purchase (or location of the kiosk) as determined by the GPS sensor 124, the date and time at which the user provided the biospecimen, etc. Each separate data element (of the provenance data and scanned code of the biospecimen) that is used to generate the first NFT is encrypted by way of a secure hash function, such as MD5, SHA-1, SHA-2 256, SHA-2 512, SHA-3, etc., to generate a hash value of the respective data element. The hash values are then used to create the first NFT.

A second NFT is created (later) to represent the extracted, residual, or corresponding bio-data after the biospecimen of the user is processed in the lab. For instance, a tiny fraction of the DNA data can be used to create a "DNA fingerprint ID" (or Self-Sovereign DNA Fingerprint) that can be used to relate the genotypic identity of the user to each of his or her bio-data sets, based on at least 50 genotyped single-nucleotide polymorphisms (SNPs) or up to 96 unique SNPs. Using the SNPs, the second NFT is created as the DNA fingerprint ID of the user, which is further hash encrypted (as noted above). An exemplary proposed list of SNPs includes, without limitation, the following SNPs: rs1471939, rs4666200, rs7554936, rs9530435, rs6104567, rs2272998, rs560681, rs6591147, rs321198, rs870347, rs2946788, rs4891825, rs10108270, rs2397060, rs7229946, rs13182883, rs1876482, rs315791, rs7205345, rs798443, rs4717865, rs2416791, rs2125345, rs4746136, rs13218440. rs1523537, rs1058083, rs1344870, rs7704770, rs1410059, rs5768007, rs260690, rs13400937, rs4918842, rs9809104, rs1821380, rs279844, rs952718, rs447818, rs13134862, rs4463276, rs3943253, rs6548616, rs731257, rs9319336, rs1019029, rs1358856, rs1823718, rs2503107, rs10236187, rs1513181, rs7657799, rs2504853, rs772262, rs3737576, rs445251, rs10488710, rs722869, rs1109037, rs3780962, rs7997709, rs4670767, rs9522149, rs4908343, rs12629908, rs1336071, rs740598, rs12997453, rs2352476, rs1554472, rs10007810, rs1760921, rs1040045, rs10496971, rs7803075, rs987640, rs6444724, rs10092491, rs735612, rs985492, rs9951171, rs3907047, rs1865680, rs525869, rs2040962, rs530501, rs2032624, rs1296819, rs316598, rs722290, rs1872575, rs18579, rs891700, rs8113143, rs1008730, rs17307398. This proposed list of SNPs is not an exclusive or exhaustive list, as other SNPs may be to create the DNA fingerprint ID.

In some embodiments, the privacy-preserving biospecimen test kit kiosk and locker 100 instructs the user to create a personal digital wallet. Specifically, after scanning the unique code (or inputting the relevant information on brand, expiration date, and code shown on the biospecimen test kit), the user is instructed to provide a telephone number and several bio-marker data items in order to generate the personal digital wallet. In addition to the user's telephone number, the user is instructed to hold up a hand with the palm of the hand facing the camera 116, which captures an image of the palm. A person's palm print is unique in comparison to all other human palms. Therefore, it can be used as a pseudo-anonymous identifier of the user. In order to protect and preserve the user's privacy, of course, the palm print data is hash encrypted. Other bio-marker data obtained from the user include a voice signature. The voice signature is captured by the microphone 114 when the user vocalizes a specific statement, as instructed on the touchscreen display 112. The captured audio clip of the voice signature is hash encrypted and used as a bio-marker of the user and as another pseudo-anonymous identifier used in creating the personal digital wallet for the user. Additionally, the user's height as detected by the height sensor 120 and the user's weight as measured by the weight scale 118 are captured, hash encrypted, and used as pseudo-anonymous identifiers for creation of the personal digital wallet. Alternatively, for maximum privacy, when user does not want to create a personal digital wallet using a telephone number, a paper wallet is created and printed or an NFC card is provided for the personal (card-based) wallet, such that the NFC card reader 128 can access the personal wallet when the user taps the NFC card against the NFC card reader 128.

After creation of the personal digital wallet (or alternatively, paper wallet or card-based wallet), the user is instructed to provide a bio-sample (such as saliva for DNA/RNA, a small waste sample for microbiome, a nasal swab sample for COVID-19, etc.) to use as the biospecimen and place into the collection tube from the biospecimen test kit. For purposes of microbiome testing, a small waste sample (such as a stool sample) may be enclosed in waste tissue or separate small container or wrapping which is able to fit within the collection tube of the biospecimen test kit. Due to the sensitivity of obtaining a waste sample, the user may therefore bring the waste sample (e.g., stool or feces) obtained from the comfort and privacy of their own home or other private place. Thus, the user seeking to find out more about their microbiome may need to take a preliminary action at home prior to purchasing the biospecimen test kit. For example, the user may review instructional material on a website or other resource that explains what waste product is needed (e.g., stool, feces), how much of the waste product is needed, and how to transport the waste product to the location of the privacy-preserving biospecimen test kit kiosk and locker 100 in a clean and safe manner. Then the user may go through the instructions to purchase a microbiome test kit and complete the requirements for providing the waste product as the biospecimen in the collection tube of the biospecimen test kit.

After collecting the biospecimen of the user in the collection tube of the biospecimen test kit, the user is instructed to replace the collection tube and/or biospecimen test kit back into the particular locker 136. In some embodiments, each locker 136 includes an internal locker sensor that detects the presence of a biospecimen test kit placed in the locker 136. Thus, when the particular locker 136 opens and the user removes the biospecimen test kit from the locker, the internal locker sensor detects an absence of the biospecimen test kit, which triggers a conditional locking mechanism to remain in an unlocked state whether or not the particular locker 136 is closed. The conditional locking mechanism changes back to a lockable state when the internal locker sensor detects that the biospecimen test kit is placed back into the particular locker 136. In some embodiments, the internal locker sensor is an IR sensor that detects presence of an object placed in the locker and attempts to scan the code of the biospecimen test kit. When the code of the biospecimen test kit is successfully scanned by the IR sensor, the conditional locking mechanism changes back to the lockable state. When the user closes the locker 136 in the lockable state, the transaction is complete (and ready to be written as a transaction in the blockchain) and the user is prevented from re-opening the particular locker 136. Additionally, the biospecimen test kit can then be delivered to the lab for processing. On the other hand, when the locker is closed without the biospecimen test kit placed back into the locker 136, the internal locker sensor detects an absence of the biospecimen test kit and the conditional locking mechanism sets the state to the unlocked state, so the particular locker 136 remains open and unlocked. Also, the transaction remains in a pending state and is not yet added to the blockchain. Furthermore, when the particular locker 136 remains open and unlocked, the biospecimen test kit cannot (yet) be delivered to the lab for processing. Thus, only when the internal locker sensor detects that the user has replaced the biospecimen test kit back into the locker 136 will the conditional locking mechanism set the locker back to the lockable state, and thus, the user will be able to close the particular locker 136 in a way that automatically locks the locker 136 shut. Then the transaction would be considered complete and ready to be added to the blockchain (and the biospecimen can then be delivered to the lab for processing).

Instead of an IR sensor, in some embodiments, the internal sensor is another type of sensor. In some embodiments, the internal sensor in the locker is an internal locker camera that captures a picture of the biospecimen test kit after the user replaces it in the locker and selects an option on the touchscreen display 112 that indicates the kit is replaced in the locker. An image analysis program running on the embedded computing device 140 then analyzes the picture captured by the internal locker camera to determine whether the biospecimen test kit was correctly replaced. The image analysis program may have a baseline image of the code and information about the biospecimen test kit which it compares to the image of the code and information (if available) on the replaced biospecimen test kit. The conditional locking mechanism would similarly set the lock state of the locker based on the results of the image analysis performed by the embedded computing device 140.

As noted above, a transaction is not completed until the locker is able to be closed and locked after the user returns the biospecimen test kit to the locker and its presence within the locker is detected by the internal locker sensor (e.g., IR senor, camera, etc.). In some embodiments, the privacy-preserving biospecimen test kit kiosk and locker 100 creates a transaction message that is electronically delivered to the user's phone or prints out a transaction receipt for users that have a paper wallet or an NFC card wallet. In some embodiments, the cellular antenna 126 of the privacy-preserving biospecimen test kit kiosk and locker 100 is used to wirelessly transmit the message to the user's phone. The transaction is also added to the blockchain. In some embodiments, the transaction receipt is printed out of the printer paper opening 130 of the privacy-preserving biospecimen test kit kiosk and locker 100. Then, after several weeks of processing by the lab, the user receives a notification message (if digital wallet was created with phone number). The notification message indicates how the user can access the resulting data of the biospecimen. Also, the second NFT is provided to the user and digital wallet, representing the biospecimen in the public blockchain. For paper receipts, the user may return to the privacy-preserving biospecimen test kit kiosk and locker 100 and enter information on the receipt (or tap their NFC card to the NFC card reader 128) to determine whether the results are ready, and if ready, how to access the resulting data of the biospecimen.

Now turning to another example, FIG. 2 conceptually illustrates a privacy-preserving biospecimen test kit purchase and personal biospecimen providing process 200 for obtaining a biospecimen test kit at a privacy-preserving biospecimen test kit kiosk and locker to provide a personal biospecimen for lab processing while capturing provenance data and protecting identity of the donor of the personal biospecimen in some embodiments. As shown in this figure, the privacy-preserving biospecimen test kit purchase and personal biospecimen providing process 200 starts when a user approaches a privacy-preserving biospecimen test kit kiosk and locker (at 205) and pushes the start button on a touchscreen display (or starts by a particular voice command to facilitate interaction with users who may not have sufficient vision or tactile/touch capabilities to interact with the touchscreen display). As described above, by reference to FIG. 1, the user may be standing on a weight scale when he or she starts interacting with the touchscreen display. From the touchscreen display (or equivalent voice interaction), the user then selects (at 210) a particular type of biospecimen test kit. Examples of biospecimen test kits include, without limitation, a DNA kit (ancestry, polygenic risk score), an RNA kit (gene expression, epigenetics), a combined DNA/RNA kit, a microbiome kit (probiotics profile), a COVID-19 test kit (SARS-CoV-2 RT-PCR), etc.

After selecting a biospecimen test kit, the privacy-preserving biospecimen test kit purchase and personal biospecimen providing process 200 of some embodiments instructs the user to select a payment method (at 215) and provide corresponding payment method details. For example, a credit card number, a cryptocurrency transfer, etc. After the user completes payment, the privacy-preserving biospecimen test kit purchase and personal biospecimen providing process 200 proceeds to the next step at which a particular locker of the privacy-preserving biospecimen test kit kiosk and locker opens (at 220). The particular locker that opens includes a biospecimen test kit that matches the particular type of biospecimen test kit selected by the user (at 210). After the particular locker opens, the user removes the biospecimen test kit from the locker. In some embodiments, instructions are displayed on the touchscreen display (or audible instructions are output from a speaker) informing the user to remove the biospecimen test kit from the particular locker. In some embodiments, a stopwatch timing module starts a timer running on the embedded computing device of the privacy-preserving biospecimen test kit kiosk and locker when the particular locker is opened. In some embodiments, the user is alerted by the touchscreen display to remove the biospecimen test kit from the particular locker after a threshold time has elapsed on the timer and the biospecimen test kit has not been removed. In some embodiments, removal of the biospecimen test kit from the particular locker is detected by the internal sensor. For instance, when the internal sensor is an IR sensor, the detected removal of the biospecimen test kit triggers an event notification that causes the embedded computing device to start the stopwatch timing module to start the timer. In some embodiments, the threshold time is configurable to any suitable time as determined for each privacy-preserving biospecimen test kit kiosk and locker. For example, a threshold time may be configured for five minutes at one kiosk installation at a particular location, and, for a different kiosk installation (at another location), the threshold time may be configured to two minutes. In addition to instructing the user to remove the biospecimen test kit form the particular locker, the touchscreen display (or equivalent audible output) instructs the user to leave the door of the particular locker open.

In some embodiments, the privacy-preserving biospecimen test kit purchase and personal biospecimen providing process 200 proceeds to the next step at which the user is instructed to use the camera of the privacy-preserving biospecimen test kit kiosk and locker to scan the code on the biospecimen test kit or type in the information on the biospecimen test kit (at 225). In some embodiments, the code includes a barcode. In some embodiments, the code includes a QR code. In some embodiments, the code includes another computer-readable encoding or design. In some embodiments, the code includes a combination of codes comprising at least the barcode and the QR code. In some embodiments, scanning the code results in a unique identifier of the biospecimen test kit being captured. In some embodiments, the unique identifier of the biospecimen test kit is different from identifiers of all other biospecimen test kits. Furthermore, scanning the code also captures a brand (or company) and expiration date of the biospecimen test kit. If a camera is unavailable or inoperable for a given privacy-preserving biospecimen test kit kiosk and locker, the user may alternatively input the information (biospecimen test kit unique identifier, brand, expiration date) by way of a virtual keyboard that is visually output onto the touchscreen display.

In some embodiments, the privacy-preserving biospecimen test kit purchase and personal biospecimen providing process 200 proceeds to the next step at which the user creates (at 230) a personal digital wallet (or "electronic wallet" or "e-wallet"). The personal digital wallet is created for the user based on at least a telephone number. In some embodiments, the personal digital wallet is created based on a telephone number provided by the user, and a plurality of bio-markers of the user including at least a height of the user that is measured by the height sensor of the privacy-preserving biospecimen test kit kiosk and locker, a weight of the user that is determined by a weight scale sensor of the privacy-preserving biospecimen test kit kiosk and locker, a palm print pattern ID ("palm ID") that is captured by the camera as an image of the user's palm and is processed by an image processing module running on the embedded computing device, and a voice signature of the user that is captured by the microphone of the privacy-preserving biospecimen test kit kiosk and locker when the user is instructed to (and the user complies) utter a word, a phrase, or a combination of words. Each of the bio-markers of the user are hashed in creation of the personal digital wallet. In this way, the privacy-preserving biospecimen test kit purchase and personal biospecimen providing process 200 and the privacy-preserving biospecimen test kit kiosk and locker 100 are able to generate a personal digital wallet for a user based on a pseudo-anonymous identification of the user without truly revealing identifying information about the user, thereby maintaining user privacy and security of personal information. However, if the user does not want a personal digital wallet created, the user may elect to get a wallet in an alternative manner. One alternative is to issue an NFC card with information that provides a secure wallet and is able to be read by the NFC card reader of the privacy-preserving biospecimen test kit kiosk and locker when sufficiently tapped at the reader. Another alternative is to issue a paper wallet to the user. When a paper wallet is selected by the user, the privacy-preserving biospecimen test kit kiosk and locker creates and prints the paper wallet, outputting the paper wallet out of the printer paper opening of the privacy-preserving biospecimen test kit kiosk and locker.

Next, the privacy-preserving biospecimen test kit purchase and personal biospecimen providing process 200 of some embodiments provides biospecimen instructions (at 235) for the user to follow on the touchscreen display (or equivalent audible output). The biospecimen instruction describe the steps for the user to provide a bio-sample as his or her biospecimen for the biospecimen test kit. For example, the instructions may describe how to open packaging of the biospecimen test kit, and inform the user to remove the collection tube and deposit the biospecimen inside the collection tube, seal, and return to the biospecimen test kit package when completed. The instructions for providing the biospecimen differ according to the type of biospecimen test kit selected by the user. By way of example, for a DNA test kit or an RNA test kit, the privacy-preserving biospecimen test kit purchase and personal biospecimen providing process 200 may instruct the user to deposit a small amount of saliva into the collection tube. For a microbiome test kit selected by the user, the privacy-preserving biospecimen test kit purchase and personal biospecimen providing process 200 may instruct the user to deposit a small amount of feces wrapped in a tissue paper into the collection tube. For a COVID-19 test kit, the privacy-preserving biospecimen test kit purchase and personal biospecimen providing process 200 may instruct the user to remove a cotton swab and extract a small nasal bio-sample on the cotton swab and to return the cotton swab to the collection tube.

When the biospecimen is obtained and collected in the collection tube of the biospecimen test kit, the privacy-preserving biospecimen test kit purchase and personal biospecimen providing process 200 moves ahead to the next step of informing the user to place the biospecimen test kit (with the biospecimen contained within the collection tube) back into the locker and to close the locker door (at 240). As noted above, the locker automatically locks when the biospecimen test kit is suitable and correctly replaced back into the locker and the door closed. However, if the door of the locker is closed before the biospecimen test kit is placed back inside, the locker does not lock, as the IR sensor (or other internal locker sensor) would fail to detect presence of the biospecimen test kit within the interior of the locker.

After the door of the locker is closed and locked (based on detectable presence of the biospecimen test kit placed within the locker and identity verification by internal locker IR sensor scan or camera capture image comparison of the code/information for the biospecimen test kit), the first NFT is created. In some embodiments, the transaction is considered completed and is therefore written to the blockchain.

In some embodiments, the privacy-preserving biospecimen test kit purchase and personal biospecimen providing process 200 then creates a message of the transaction to send to the user's phone or prints a receipt of the transaction (at 245) when the user has not provided a telephone number or otherwise opted to create a paper wallet or NFC card wallet. The message or receipt includes information about the first NFT.

In some embodiments, the privacy-preserving biospecimen test kit purchase and personal biospecimen providing process 200 waits for the lab to process the biospecimen. After several weeks (approximately six-ten weeks later), the privacy-preserving biospecimen test kit purchase and personal biospecimen providing process 200 sends the user a notification message (if digital wallet was created with phone number). The notification message indicates how the user can access the resulting data of the biospecimen. Also, the second NFT is created and provided to the user and digital wallet, representing the biospecimen in the public blockchain. For paper receipts, the user may return to the privacy-preserving biospecimen test kit kiosk and locker and type in the information appearing on the transaction receipt (or tap their NFC card to the NFC card reader on the kiosk) to determine whether the results are ready, and if ready, how to access the resulting data of the biospecimen. Then the privacy-preserving biospecimen test kit purchase and personal biospecimen providing process 200 ends.

By way of example, FIG. 3 conceptually illustrates a top view of a biospecimen test kit 300 that is stored in a locker of the privacy-preserving biospecimen test kit kiosk and locker. As shown in this figure, the biospecimen test kit 300 is packaged closed with a front label 310 displayed on an outer surface of the biospecimen test kit 300 packaging.

By way of example, FIG. 4 conceptually illustrates a top view of a unique scannable code 400 associated with the biospecimen test kit 300 shown in FIG. 3. As shown in this figure, the biospecimen test kit 300 packaging is open, which reveals the code 400 disposed along an inner surface of a top lid of the packaging. The open packaging of the biospecimen test kit 300 also reveals a biospecimen collection tube 410 which is used to collect a biospecimen sample (such as a saliva sample) of the user.

By way of another example, FIG. 5 conceptually illustrates a rear perspective view of a biospecimen collection tube 410 with a collection tube identifying sticker 500 affixed to an outer surface of the biospecimen collection tube 410. As shown in this figure, the collection tube identifying sticker 500 includes a bar code, an expiration data, a brand, and a numeric code which can be typed into the touchscreen display 112 by the user (or audibly spoken into the microphone 114) when prompted by the privacy-preserving biospecimen test kit kiosk and locker 100.

While not shown in FIG. 3, in some embodiments, the biospecimen test kit 300 packaging may also include the scannable code 400 and the identifying sticker 500 with information such as expiration date, brand, and a numeric or alpha-numeric code that is the unique ID of the biospecimen test kit 300.

To make the privacy-preserving biospecimen test kit kiosk and locker of the present disclosure, one of the essential components is a blockchain, because all of the data is referenced to the user's blockchain address. The blockchain may be a particular blockchain implementation (such as, but not limited to, Ethereum blockchain). In some embodiments, the blockchain is a public blockchain and the transactions involved with obtaining a biospecimen test kit, providing a biospecimen, and processing the biospecimen at the lab are encrypted (by secure hash algorithm/function) and added to blocks of the blockchain. In this way, a chain of transactions for the biospecimen and resulting data set (after processing of the biospecimen) are publicly available. Since blockchain provides a distributed ledger of these transactions, the implementation is suitable for international or cross-country or border applications, regardless of the data privacy laws in such countries or jurisdictions. The nature of blockchain being immutable also guarantees that tracing of the transactions can be accomplished with a level of certainty that may be desirable for certain users. For instance, in some countries, each person is entitled to control their personal data, and thus, can request that a company delete all data it has related to the person. The blockchain ensures that all touches of such data are accounted for, yet none of the blockchain information includes any full set of user information. For example, no transaction of the blockchain stores the user's DNA sequence data (say, if the user purchased a DNA biospecimen test kit). At most, the DNA fingerprint ID is encrypted and stored, as well as other transaction information. By employing cryptographic technology, public key infrastructure, and blockchain technology with commercially available biospecimen test kits obtained from a privacy-preserving biospecimen test kit kiosk and locker, users are able to effectively relate, claim ownership, consent to use, and keep track of biospecimen data and the resulting data (after processing of biospecimen samples such as saliva, stool/feces, nasal mucus, tissue samples, cells, etc.) in a way that is safe, secure, convenient, and private, and without ever being required to disclose the user's own personal identifying information.

By way of example, FIG. 6 conceptually illustrates a block diagram of a mobile device 600 with a personal digital wallet for a user of the privacy-preserving biospecimen test kit kiosk and locker in some embodiments. As shown in this figure, the mobile device 600 includes a bus 610, a random access memory (RAM) 620, a main control unit (MCU) 630 for runtime processing to access, view, and interact with a personal digital wallet created for the user, a code execution unit 640 embedded within the MCU 630, a first persistent flash memory 650 that stores a personal digital wallet application and storage for the personal digital wallet and its contents (such as non-fungible tokens, cryptocurrency, etc.), a second persistent flash memory 660 that stores encryption protocol code that is executed by code execution unit 640 of the MCU 630 to decrypt the hash encrypted data representing the post-processed biospecimen results of the user and access the contents of the personal digital wallet by way of the personal digital wallet application that is stored in the first persistent flash memory 650, radio (RF) hardware 670 to transmit and receive cellular signals and other wireless data signals, a touchscreen and input/output (I/O) management unit 680, and a global positioning system (GPS) receiver 690.

Many of the above-described features and applications of the wireless activity and environmental monitoring device and system for small, caged mammals are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

FIG. 7 conceptually illustrates an electronic system 700 with which some embodiments of the invention are implemented. The electronic system 700 may be a computer, such as the embedded computing device 140 described above, by reference to FIG. 1, or any other sort of electronic computing device. Such an electronic system 700 includes various types of computer readable media and interfaces for various other types of computer readable media. Specifically, the electronic system 700 includes a bus 705, processing unit(s) 710, a system memory 715, a read-only 720, a permanent storage device 725, sensor input devices 730, output devices 735, and a network 740.

The bus 705 collectively represents all system, peripheral, and chipset buses that communicatively connect the numerous internal devices of the electronic system 700. For instance, the bus 705 communicatively connects the processing unit(s) 710 with the read-only memory 720, the system memory 715, and the permanent storage device 725.

From these various memory units, the processing unit(s) 710 retrieves instructions to execute and data to process in order to execute the processes of the invention. The processing unit(s) may be a single processor or a multi-core processor in different embodiments.

The read-only-memory (ROM) 720 stores static data and instructions that are needed by the processing unit(s) 710 and other modules of the electronic system. The permanent storage device 725, on the other hand, is a read-and-write memory device. This device is a non-volatile memory unit that stores instructions and data even when the electronic system 700 is off. Some embodiments of the invention use a mass-storage device (such as a magnetic or optical disk and its corresponding disk drive) as the permanent storage device 725.

Other embodiments use a removable storage device (such as a floppy disk or a flash drive) as the permanent storage device 725. Like the permanent storage device 725, the system memory 715 is a read-and-write memory device. However, unlike storage device 725, the system memory 715 is a volatile read-and-write memory, such as a random access memory. The system memory 715 stores some of the instructions and data that the processor needs at runtime. In some embodiments, the invention's processes are stored in the system memory 715, the permanent storage device 725, and/or the read-only memory 720. For example, the various memory units include instructions for processing appearance alterations of displayable characters in accordance with some embodiments. From these various memory units, the processing unit(s) 710 retrieves instructions to execute and data to process in order to execute the processes of some embodiments.

The bus 705 also connects to the sensor input devices 730 and the output devices 735. The sensor input devices 730 capture some environmental provenance data, some user-specific bodily information that provides pseudo-anonymous identification data for creation of a personal digital wallet by the electronic system 700, and detect other information in and around each installed privacy-preserving biospecimen test kit kiosk and locker. The sensor input devices 730 include a weight scale, a height sensor, an air quality sensor, a global positioning system (GPS) sensor, a humidity sensor, a temperature sensor, and internal locker detection sensors. In some embodiments, one or more of the internal locker detection sensors is an infrared (IR) sensor. In some embodiments, the sensor input devices 730 further include non-sensory, information capturing devices including a camera and a microphone. In some embodiments, one or more of the internal locker detection sensors is a camera. The output devices 735 display images, textual information, and other graphical information generated by the electronic system 700. The output devices 735 include printers, such as a printer that is embedded within the privacy-preserving biospecimen test kit kiosk and locker and outputs printed paper through the printer paper opening described above by reference to FIG. 1. The output devices 735 also include display devices. In some embodiments, the output display devices 735 include a touchscreen, such as the touchscreen display 112 described above by reference to FIG. 1, which functions as both an input and output device.

Finally, as shown in FIG. 7, bus 705 also couples electronic system 700 to a network 740 through a network adapter (not shown) or a cellular antenna, such as the cellular antenna 126 described above, by reference to FIG. 1. In this manner, the computer can be a part of a network of computers (such as a local area network ("LAN"), a wide area network ("WAN"), or an intranet), a network of networks (such as the Internet), or a cellular network. Any or all components of electronic system 700 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A privacy-preserving biospecimen test kit kiosk and locker that stores retrieved data in a private digital wallet comprising:
    a plurality of locker boxes that each store a biospecimen test kit for purchase by a user who intends to maintain anonymity while providing a personal biospecimen to a biospecimen processing lab without revealing personal identity;
    a touchscreen that guides the user through a process of purchasing a particular type of biospecimen test kit and collecting the personal biospecimen in the biospecimen test kit purchased by the user, wherein the particular type of biospecimen test kit purchased by the user comprises one or more of a DNA kit, a RNA kit, a microbiome kit, and a COVID-19 kit;
    a camera that is used to scan a unique encoding on the biospecimen test kit purchased by the user;
    an air quality sensor that detects nearby air quality and includes air quality data as detected in a set of provenance data associated with the personal biospecimen provided by the user and collected in the biospecimen test kit purchased by the user;
    a temperature sensor that measures nearby temperature and includes temperature data as measured in the set of provenance data associated with the personal biospecimen provided by the user and collected in the biospecimen test kit purchased by the user;
    a humidity sensor that detects surrounding humidity and includes humidity data as detected in the set of provenance data associated with the personal biospecimen provided by the user and collected in the biospecimen test kit purchased by the user;
    a GPS sensor that calculates a present location and includes GPS location data as calculated in the set of provenance data associated with the personal biospecimen provided by the user and collected in the biospecimen test kit purchased by the user;
    a non-fungible token (NFT) associated with a public blockchain and which represents the personal biospecimen of the user and is created to include the set of provenance data associated with the personal biospecimen provided by the user and information from the unique encoding scanned on the biospecimen test kit purchased by the user;
    a printer that prints out a confirmation of a transaction for the purchase of the biospecimen test kit, the collection of the personal biospecimen in the biospecimen test kit, and the creation of the NFT, wherein the printer prints out the confirmation after the user places the biospecimen test kit with the collected personal biospecimen into a particular locker box in the plurality of locker boxes from which the user obtained the biospecimen test kit after purchase, wherein the transaction is written to a block in the public blockchain;
    a metal outer kiosk body that houses each of the plurality of locker boxes, the touchscreen, the camera, the printer, the GPS sensor, the air quality sensor, the humidity sensor, and the temperature sensor; and
    a base platform upon which the metal outer kiosk body stands.

2. The privacy-preserving biospecimen test kit kiosk and locker of claim 1 further comprising a plurality of internal locker sensors with the plurality of locker boxes, wherein each internal lock sensor detects presence of a biospecimen test kit after biospecimen collection and replacement of the biospecimen test kit within the locker box.

3. The privacy-preserving biospecimen test kit kiosk and locker of claim 1, wherein the touchscreen further guides the user through a process of creating a personal digital wallet for the user based on at least a telephone number of a mobile device of the user.

4. The privacy-preserving biospecimen test kit kiosk and locker of claim 3, wherein the camera further captures an image of a palm print of the user that is hash encrypted and included in a set of pseudo-anonymous identification of the user in order to create the personal digital wallet.

5. The privacy-preserving biospecimen test kit kiosk and locker of claim 4 further comprising a weight scale disposed over the base platform, wherein the weight scale measures weight of the user, wherein weight data of the user as measured by the weight scale is hash encrypted and included in the set of pseudo-anonymous identification of the user in order to create the personal digital wallet.

6. The privacy-preserving biospecimen test kit kiosk and locker of claim 4 further comprising a height meter sensor embedded between a pair of locker boxes, wherein the height meter sensor measures height of the user, wherein height data of the user as measured by the height meter sensor is hash encrypted and included in the set of pseudo-anonymous identification of the user in order to create the personal digital wallet.

7. The privacy-preserving biospecimen test kit kiosk and locker of claim 4 further comprising a microphone that captures a voice signature of the user when the user vocalizes one or more words as instructed by the touchscreen during the process of creating the personal digital wallet for the user, wherein the voice signature is captured as a voice signature audio clip that is hash encrypted and included in the set of pseudo-anonymous identification of the user in order to create the personal digital wallet.

8. The privacy-preserving biospecimen test kit kiosk and locker of claim 1, wherein the unique encoding on the biospecimen test kit scanned by the camera includes a unique biospecimen test kit identifier, a brand associated with the biospecimen test kit, and an expiration date.

9. The privacy-preserving biospecimen test kit kiosk and locker of claim 1 further comprising an embedded computing device comprising a central processing unit (CPU), data storage, a memory module, and a plurality of input devices that receive touch input of the user when the user makes touch gestures on the touchscreen, camera scanning and image capture data from the camera, and sensor data captured from the air quality sensor, the humidity sensor, and the temperature sensor.

10. The privacy-preserving biospecimen test kit kiosk and locker of claim 1 further comprising a near field communication (NFC) card reader that provides access to a pre-established private locker box for users who do not understand blockchain and is associated with a pre-established NFC card wallet.

* * * * *